(12) United States Patent
Clark et al.

(10) Patent No.: US 10,031,111 B2
(45) Date of Patent: Jul. 24, 2018

(54) METHODS AND APPARATUS FOR MACHINING OBJECTS

(71) Applicant: ROLLS-ROYCE plc, London (GB)

(72) Inventors: Daniel Clark, Derby (GB); David C. Wright, Loughborough (GB)

(73) Assignee: ROLLS-ROYCE plc, London (GB)

( * ) Notice: Subject to any disclaimer, the term of this patent is extended or adjusted under 35 U.S.C. 154(b) by 79 days.

(21) Appl. No.: 15/346,458

(22) Filed: Nov. 8, 2016

(65) Prior Publication Data

US 2017/0160241 A1    Jun. 8, 2017

(30) Foreign Application Priority Data

Dec. 3, 2015   (GB) .................................. 1521350.7

(51) Int. Cl.
*B24C 1/04*      (2006.01)
*G01N 29/32*    (2006.01)
(Continued)

(52) U.S. Cl.
CPC ........... *G01N 29/326* (2013.01); *B24C 1/045* (2013.01); *G01B 17/02* (2013.01); *G01N 29/043* (2013.01);
(Continued)

(58) Field of Classification Search
CPC .... G01N 29/326; G01N 29/043; G01N 29/07; G01N 29/225; G01N 29/226; G01N 29/4427; G01N 2291/011; G01N 2291/0231; G01N 2291/02854; B24C 1/045; B23Q 17/20; B23Q 17/22; Y10T 409/303752; Y10T 409/303808
(Continued)

(56) References Cited

U.S. PATENT DOCUMENTS

| 4,541,281 A | * | 9/1985 | Chubachi | ............... | G01H 3/125 |
| | | | | | 73/602 |
| 4,574,637 A | * | 3/1986 | Adler | .................... | G01N 29/00 |
| | | | | | 73/599 |

(Continued)

FOREIGN PATENT DOCUMENTS

EP    2 860 521 A1    4/2015

OTHER PUBLICATIONS

May 23, 2016 Search Report issued in British Patent Application No. GB1521350.7.

(Continued)

*Primary Examiner* — George Nguyen
(74) *Attorney, Agent, or Firm* — Oliff PLC (57) ABSTRACT

A method of machining an object, the method comprising: receiving a signal from an ultrasonic transducer; determining at least a first external surface of the object and a second internal surface of the object in the received signal; determining a thickness between the first external surface and the second internal surface of the object, the object comprising a first material between the first external surface and the second internal surface, and a second material between the second internal surface and a third surface, the determination of the thickness using a database including a plurality of materials and a plurality of associated acoustic wave velocities; and controlling machining of the first external surface using the determined thickness.

14 Claims, 8 Drawing Sheets (51) Int. Cl.
*G01N 29/04* (2006.01)
*G01N 29/07* (2006.01)
*G01B 17/02* (2006.01)
*G01N 29/22* (2006.01)
*G01N 29/44* (2006.01)

(52) U.S. Cl.
CPC ........... *G01N 29/07* (2013.01); *G01N 29/225* (2013.01); *G01N 29/226* (2013.01); *G01N 29/4427* (2013.01); *G01N 2291/011* (2013.01); *G01N 2291/0231* (2013.01); *G01N 2291/02854* (2013.01)

(58) Field of Classification Search
USPC .......................................................... 451/2
See application file for complete search history.

(56) References Cited

U.S. PATENT DOCUMENTS

| | | | | |
|---|---|---|---|---|
| 4,730,494 A * | 3/1988 | Ishikawa | .............. | G01B 17/025 73/606 |
| 5,254,900 A * | 10/1993 | Magori | ................ | B06B 1/0644 310/322 |
| 5,349,862 A * | 9/1994 | Chubachi | ................. | G01H 5/00 73/602 |
| 6,363,787 B1 | 4/2002 | Carlson et al. | | |
| 7,650,790 B2 * | 1/2010 | Wright | ............... | G01N 27/9026 702/35 |
| 7,677,101 B2 * | 3/2010 | Xu | ........................ | G01N 29/022 73/597 |
| 9,630,248 B2 * | 4/2017 | Wright | ..................... | B22F 3/15 |
| 2006/0266119 A1 * | 11/2006 | Cobb | ..................... | G01N 29/07 73/579 |
| 2007/0020135 A1 * | 1/2007 | Jackson | .................... | B22F 3/14 419/29 |
| 2010/0263450 A1 * | 10/2010 | Bobrek | ..................... | B22F 3/15 73/622 |
| 2011/0038748 A1 * | 2/2011 | Channel | ................ | C22C 1/0433 419/8 |
| 2014/0260625 A1 * | 9/2014 | Escobar-Ruiz | .... | G01N 29/4454 73/588 |
| 2015/0098854 A1 * | 4/2015 | Wright | ..................... | B22F 3/15 419/8 |

OTHER PUBLICATIONS

Schmitt, Robert et. al. "Ultrasonic Sensor Tool for Automated Material Inspection in Milling Machines". ECNDT, pp. 1-8, 2006.

* cited by examiner

METHODS AND APPARATUS FOR MACHINING OBJECTS

TECHNOLOGICAL FIELD

The present disclosure concerns methods and apparatus for machining objects. The present disclosure may also concern methods and apparatus for inspecting objects.

BACKGROUND

In various industries, objects may be formed from two or more different materials (such as two different alloys). For example, an object may be bimetallic and comprise a first metallic material and a second different metallic material that at least partially envelopes and covers the first metallic material. Hot pressing, or hot isostatic pressing, may be used to manufacture such an object by consolidating and diffusion bonding powder material together to form the object. Additionally, hot pressing, or hot isostatic pressing may be used to diffusion bond two or more objects together to form a single object.

Hot isostatic pressing of powder materials to manufacture an article involves initially forming a canister which defines the shape of the object to be manufactured. The canister is filled with powder material, evacuated to remove gases from the canister, and then sealed. The sealed canister is then hot isostatically pressed to consolidate the powder material within the canister and to diffusion bond the powder material together to form the article. During the hot isostatic pressing process the particles of the powder material are initially deformed to fill the inter-particle spaces, or voids, and then the particles of the powder material are diffusion bonded together. The canister is then removed from the article, typically by machining, by dissolving the canister in acid, or by a combination of machining and dissolving in acid.

One problem associated with the use of acids to dissolve and thereby remove the canister is that they may be precluded by environmental legislation. A further problem associated with acids is that the acids used to remove the canister may also cause damage to the article.

One problem associated with machining is that the use of machining to remove the canister may result in damage to the article and/or machining tool because the position of the interface between the canister and the article and the positions of features of the article are not known after the hot pressing process, or hot isostatic pressing process. The position of the interface between the canister and the article after consolidation of the powder material is not known accurately because of process variations in the shrinkage of the particles of the powder material and the collapse of the canister as the inter-particle spaces, or voids, are filled by the deformation of the particles of the powder material.

BRIEF SUMMARY

According to various examples there is provided a method of machining an object, the method comprising: receiving a signal from an ultrasonic transducer; determining at least a first external surface of the object and a second internal surface of the object in the received signal; determining a thickness between the first external surface and the second internal surface of the object, the object comprising a first material between the first external surface and the second internal surface, and a second material between the second internal surface and a third surface, the determination of the thickness using a database including a plurality of materials and a plurality of associated acoustic wave velocities; and controlling machining of the first external surface using the determined thickness.

The method may further comprise: determining the third surface of the object in the received signal; and determining a thickness between the second internal surface and the third surface using the database.

The third surface may be an external surface of the object.

The third surface may be an internal surface of the object.

The database may further comprise a plurality of temperatures for at least some of the plurality of materials, the plurality of acoustic wave velocities being associated with the plurality of temperatures.

The method may further comprise: receiving a sensed temperature of the object; and selecting an acoustic wave velocity from the plurality of acoustic wave velocities using the received sensed temperature to determine the thickness between the first external surface and the second internal surface.

The object may be at least partially immersed in a liquid, the method may further comprise: controlling a heat transfer device to maintain the liquid at a predetermined temperature, the acoustic wave velocities in the database being acoustic wave velocities in the plurality of materials at the predetermined temperature.

The method may further comprise receiving a user input signal including information identifying at least the first material and the second material of the object.

Controlling machining of the first external surface may include controlling a tool to remove at least a part of the first material from the object.

Controlling machining of the first external surface may include controlling a water jet cutter to machine the object. The ultrasonic transducer may be integrated with the water jet cutter.

The object may be formed using a hot isostatic pressing process.

According to various examples there is provided a method of inspecting an object, the method comprising: receiving a signal from an ultrasonic transducer; determining at least a first external surface of the object and a second internal surface of the object in the received signal; and determining a thickness between the first external surface and the second internal surface of the object, the object comprising a first material between the first external surface and the second internal surface, and a second material between the second internal surface and a third surface, the determination of the thickness using a database including a plurality of materials and a plurality of associated acoustic wave velocities.

The method may further comprise generating a model of the object using at least the determined thickness.

According to various examples there is provided a computer program that, when read by a computer, causes performance of the method as described in any of the preceding paragraphs.

According to various examples there is provided a non-transitory computer readable storage medium comprising computer readable instructions that, when read by a computer, cause performance of the method as described in any of the preceding paragraphs.

According to various examples there is provided apparatus comprising a controller configured to perform the method as described in any of the preceding paragraphs.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

BRIEF DESCRIPTION

Embodiments will now be described by way of example only, with reference to the Figures, in which.

DETAILED DESCRIPTION

In the following description, the terms 'connected' and 'coupled' mean operationally connected and coupled. It should be appreciated that there may be any number of intervening components between the mentioned features, including no intervening components.

Figure 1:
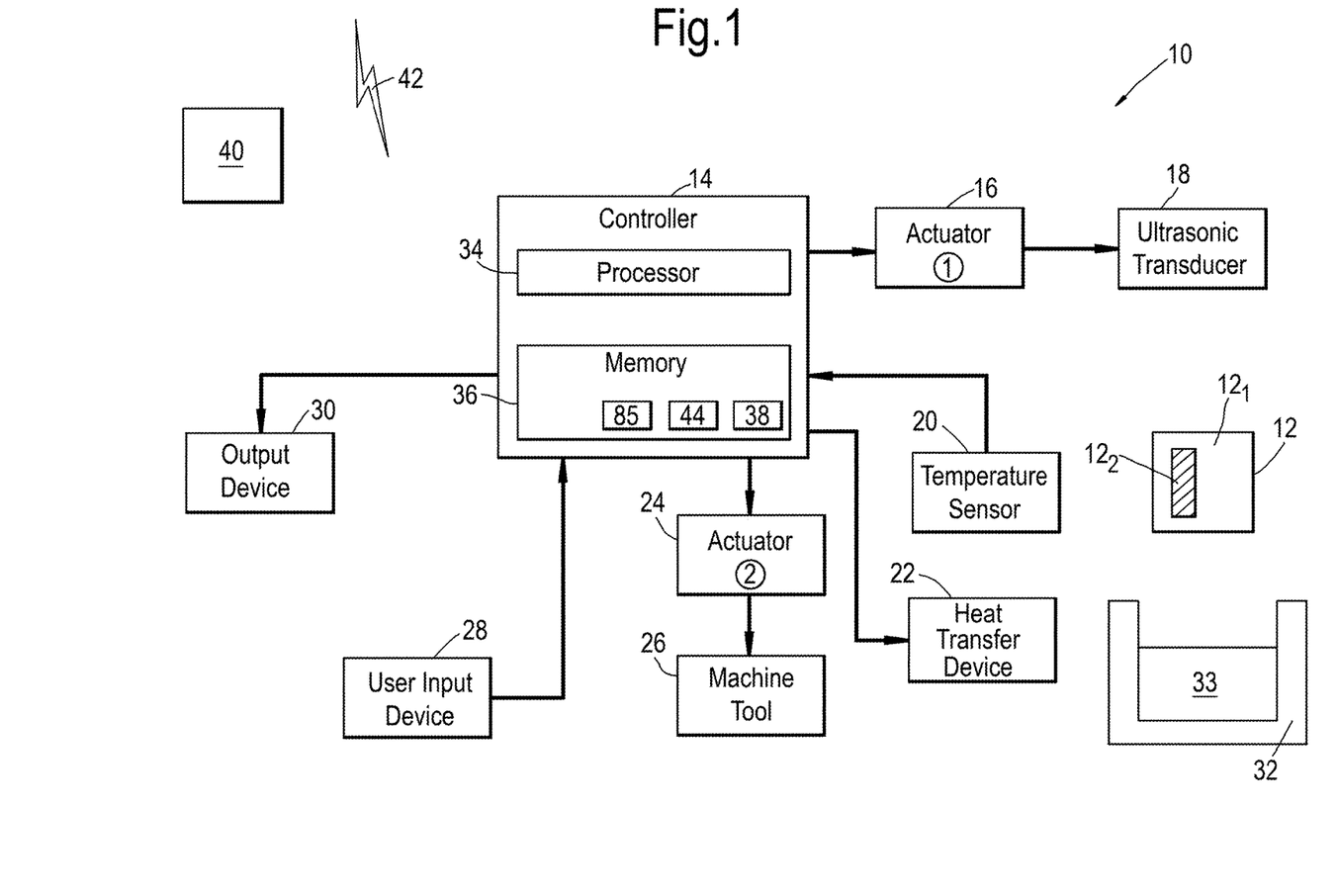
FIG. 1 illustrates a schematic diagram of apparatus for machining an object according to various examples.

FIG. 1 illustrates a schematic diagram of an apparatus 10 for machining an object 12 according to various examples. The apparatus 10 includes a controller 14, a first actuator 16, an ultrasonic transducer 18, a temperature sensor 20, a heat transfer device 22, a second actuator 24, a machine tool 26, a user input device 28, an output device 30 and a container 32. In summary, the apparatus 10 may be configured to inspect the object 12 to determine the internal structure of the object 12 and then use the determined internal structure to machine the object 12.

In some examples, the apparatus 10 may be a module. As used herein, the wording 'module' refers to a device or apparatus where one or more features are included at a later time, and possibly, by another manufacturer or by an end user. For example, where the apparatus 10 is a module, the apparatus 10 may only include the controller 14, and the remaining features may be added by another manufacturer, or by an end user.

The controller 14, the first actuator 16, the ultrasonic transducer 18, the temperature sensor 20, the heat transfer device 22, the actuator 24, the machine tool 26, the user input device 28 and the output device 30 may be coupled to one another via a wireless link and may consequently comprise transceiver circuitry and one or more antennas. Additionally or alternatively, the controller 14, the first actuator 16, the ultrasonic transducer 18, the temperature sensor 20, the heat transfer device 22, the actuator 24, the machine tool 26, the user input device 28 and the output device 30 may be coupled to one another via a wired link and may consequently comprise interface circuitry (such as a Universal Serial Bus (USB) socket). It should be appreciated that the controller 14, the first actuator 16, the ultrasonic transducer 18, the temperature sensor 20, the heat transfer device 22, the actuator 24, the machine tool 26, the user input device 28 and the output device 30 may be coupled to one another via any combination of wired and wireless links.

The object 12 may be any component or article that includes at least two different materials. The object 12 may be an intermediate product of a manufacturing process that may be further processed to provide a final product. For example, the object 12 may be an intermediate product of a hot pressing or a hot isostatic pressing process where the object 12 includes the component being manufactured, and the canister for forming the component. The object 12 includes: a first material $12_1$ between a first external surface and a second internal surface; and a second material $12_2$ between the second internal surface and a third surface (which may be an internal surface of the object 12, or may be an external surface of the object 12).

The controller 14 may comprise any suitable control circuitry to cause performance of the methods described herein and as illustrated in FIGS. 6, 9, 10, and 11. The controller 14 may comprise: at least one application specific integrated circuit (ASIC); and/or at least one field programmable gate array (FPGA); and/or single or multi-processor architectures; and/or sequential (Von Neumann)/parallel architectures; and/or at least one programmable logic controllers (PLCs); and/or at least one microprocessor; and/or at least one microcontroller; and/or a central processing unit (CPU); and/or a graphics processing unit (GPU), to perform the methods.

In various examples, the controller 14 may comprise at least one processor 34 and at least one memory 36. The memory stores a computer program 38 comprising computer readable instructions that, when read by the processor 34, causes performance of the methods described herein, and as illustrated in FIGS. 6, 9, 10 and 11. The computer program 38 may be software or firmware, or may be a combination of software and firmware.

The processor 34 may include at least one microprocessor and may comprise a single core processor, may comprise multiple processor cores (such as a dual core processor or a quad core processor), or may comprise a plurality of processors (at least one of which may comprise multiple processor cores).

The memory 36 may be any suitable non-transitory computer readable storage medium, data storage device or devices, and may comprise a hard disk drive (HDD) and/or solid state memory (SDD) (such as flash memory). The memory 36 may be permanent non-removable memory, or may be removable memory (such as a universal serial bus (USB) flash drive).

The computer program 38 may be stored on a non-transitory computer readable storage medium 40. The computer program 38 may be transferred from the non-transitory computer readable storage medium 40 to the memory 36. The non-transitory computer readable storage medium 40 may be, for example, a USB flash drive, an optical disk (such as a compact disc (CD), a digital versatile disc (DVD) or a Blu-ray disc) or a secure digital (SD) card. In some examples, the computer program 38 may be transferred to the memory via a signal 42 (such as a wireless signal or a wired signal).

The memory 36 also stores a database 44 that is described in greater detail in the following paragraphs with reference to FIGS. 2 and 3.

The first actuator 16 is configured to move the ultrasonic transducer 18 relative to the object 12. For example, the first actuator 16 may be configured to move the ultrasonic transducer 18 so that the ultrasonic transducer 18 has six degrees of freedom (For example, movement in X, Y, Z, pitch, yaw, and roll). The first actuator 16 may comprise any suitable mechanism for moving the ultrasonic transducer 18 and may, for example, comprise one or more servo-motors. The controller 14 is configured to control the first actuator 16 to move the ultrasonic transducer 18 relative to the object 12. In some examples, the apparatus 10 may not comprise the first actuator 16 and instead, the ultrasonic transducer 18 may be moved manually by an operator.

The ultrasonic transducer 18 may comprise any suitable circuitry configured to convert ultrasonic waves into electrical signals. For example, the ultrasonic transducer 18 may be a piezoelectric transducer or a capacitive transducer. In some examples, the ultrasonic transducer 18 may only comprise an ultrasonic receiver. In other examples, the ultrasonic transducer 18 may comprise an ultrasonic transmitter and an ultrasonic receiver (that is, the ultrasonic transducer 18 is an ultrasonic transceiver). The controller 14 is configured to receive signals from the ultrasonic transducer 18.

In some examples, the ultrasonic transducer 18 may be configured to project a jet of liquid onto the object 12. For example, the ultrasonic transducer 18 may include (or be coupled to) a nozzle and a conduit connected to a supply of liquid (such as water). The ultrasonic transducer 18 may be configured to transmit ultrasonic waves into the object 12 via the jet of liquid.

The temperature sensor 20 may comprise any suitable thermometer that is configured to sense the temperature of the object 12 or the liquid 33 in the container 32 (in examples where the object 12 is at least partially immersed in the liquid 33). For example, the temperature sensor 20 may include an infrared thermometer, a thermistor or a thermocouple. The controller 14 is configured to receive the sensed temperature from the temperature sensor 20.

The heat transfer device 22 is configured to maintain the liquid 33 in the container 32 at a predetermined temperature. The heat transfer device 22 may include any suitable mechanism for controlling the temperature of the liquid and may comprise a refrigeration unit and/or a heater (such as an immersion heater). The controller 14 is configured to control the heat transfer device 22 to maintain the temperature of the liquid 33 at the predetermined temperature.

The second actuator 24 is configured to move the machine tool 26 relative to the object 12. For example, the second actuator 24 may be configured to move the machine tool 26 so that the machine tool 26 has six degrees of freedom (For example, movement in X, Y, Z, pitch, yaw, and roll). The second actuator 24 may comprise any suitable mechanism for moving the machine tool 26 and may, for example, comprise one or more servo-motors. The controller 14 is configured to control the second actuator 24 to move the machine tool 26 relative to the object 12.

The machine tool 26 may comprise any suitable tool or tools for machining the object 12. In various examples, the machine tool 26 may comprise a water jet cutter to machine the object 12. The ultrasonic transducer 18 may be integrated with the water jet cutter and consequently, the apparatus 10 may comprise only one of the first actuator 16 and the second actuator 24 (in other words, the ultrasonic transducer 18 and the machine tool 26 may be moved by the same actuator). In other examples, the machine tool 26 may comprise a milling tool, a linishing tool, or a grinding tool. The controller 14 may be configured to control the operation of the machine tool 26.

The user input device 28 may comprise any suitable device for enabling an operator to at least partially control the apparatus 10. For example, the user input device 28 may comprise one or more of a keyboard, a keypad, a touchpad, a touchscreen display, a computer mouse, and a joystick. The controller 14 is configured to receive signals from the user input device 28.

The output device 30 may be any suitable device for conveying information to an operator. For example, the output device 30 may comprise a display (such as a liquid crystal display, or a light emitting diode display, or an active matrix organic light emitting diode display, or a thin film transistor display, or a cathode ray tube display), and/or a printer (such as an inkjet printer or a laser printer). The controller 14 is arranged to provide a signal to the output device 30 to cause the output device 30 to convey information to the operator.

The apparatus 10 may operate in three configurations. In the first configuration, the object 12 is positioned within the container 32 and is at least partially immersed in the liquid 33 contained by the container 32. The ultrasonic transducer 18 receives ultrasonic waves without the use of the jet of liquid mentioned above. In the second configuration, the object 12 is positioned within the container 32 and is at least partially immersed in the liquid 33 contained by the container 32. The ultrasonic transducer 18 receives ultrasonic waves using the jet of liquid mentioned above. In a third configuration, the object 12 is positioned within the container 32 (or positioned on a support) and is not immersed in the liquid 33 (that is, the container 32 does not contain the liquid 33). The ultrasonic transducer 18 receives ultrasonic waves using the jet of liquid mentioned above.

Figure 2:
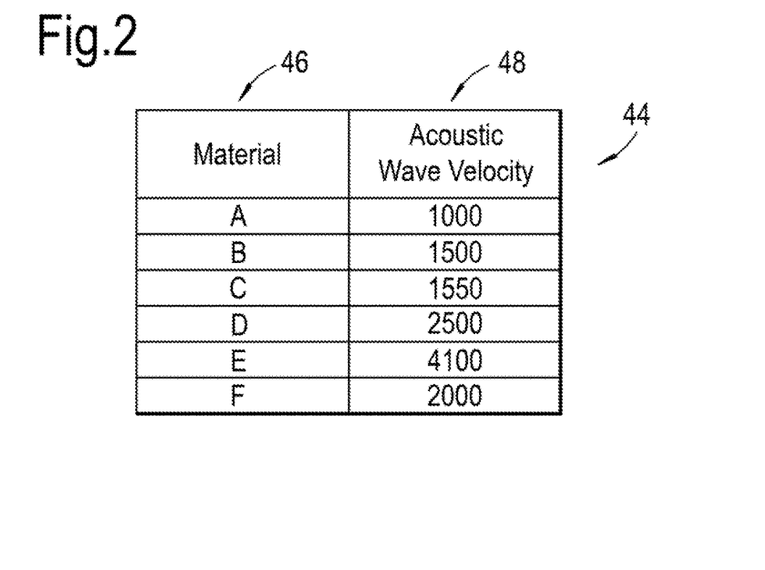
FIG. 2 illustrates a database in a tabular format according to various examples.

FIG. 2 illustrates a database 44 according to various examples. The database 44 is shown as a table in FIG. 2 for illustrative purposes. It should be appreciated that in other examples, the database 44 may be coded and stored in an alternative structure in the memory 36.

The database 44 includes a first column 46 for material and a second column 48 for acoustic wave velocity in the associated material. The acoustic wave velocity in the associated material is at a predetermined temperature (since acoustic wave velocity varies with the temperature of the material). Material A has an associated acoustic wave velocity of 1000 meters per second, material B has an associated acoustic wave velocity of 1500 meters per second, material C has an associated acoustic wave velocity of 1550 meters per second, material D has an associated acoustic wave velocity of 2500 meters per second, material E has an associated acoustic wave velocity of 4100 meters per second, and material F has an associated acoustic wave velocity of 2000 meters per second.

Figure 3:
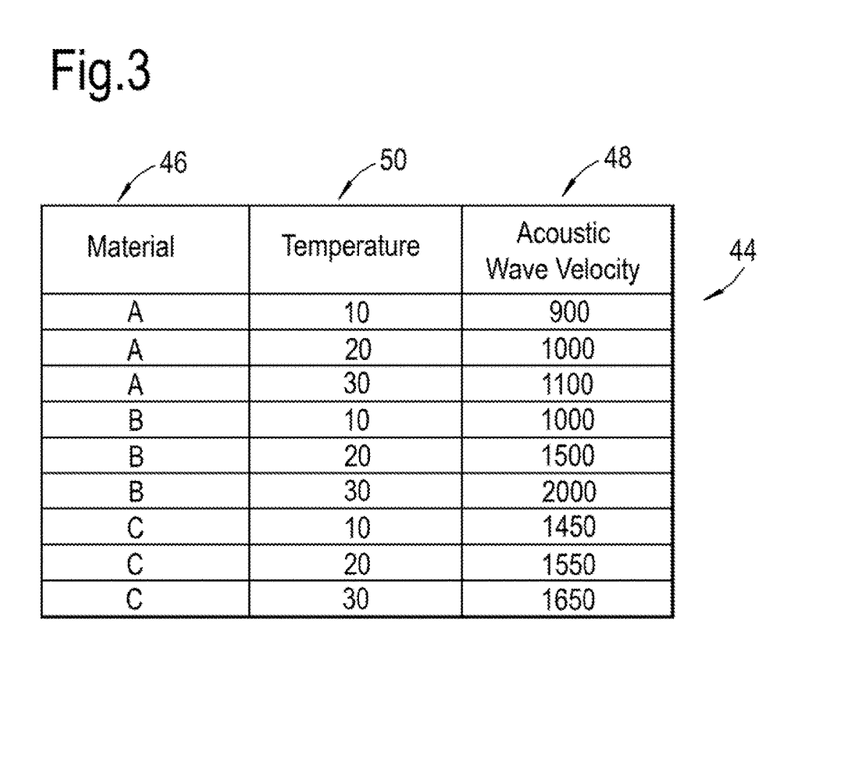
FIG. 3 illustrates another database in a tabular format according to various examples.

FIG. 3 illustrates another database 44 according to various examples. Once again, the database 44 is shown as a table in FIG. 3 for illustrative purposes. It should be appreciated that in other examples, the database 44 may be coded and stored in an alternative structure in the memory 36.

The database 44 includes a first column 46 for material, a second column 50 for temperature, and a third column 48 for acoustic wave velocity in the associated material at the associated temperature. Material A has an associated acoustic wave velocity of 900 meters per second at 10 Celsius, an associated acoustic wave velocity of 1000 meters per second at 20 Celsius, and an associated acoustic wave velocity of 1100 meters per second at 30 Celsius. Material B has an associated acoustic wave velocity of 1000 meters per second at 10 Celsius, an associated acoustic wave velocity of 1500 meters per second at 20 Celsius, and an associated acoustic wave velocity of 2000 meters per second at 30 Celsius. Material C has an associated acoustic wave velocity of 1450 meters per second at 10 Celsius, an associated acoustic wave velocity of 1550 meters per second at 20 Celsius, and an associated acoustic wave velocity of 1650 meters per second at 30 Celsius.

Figure 4:
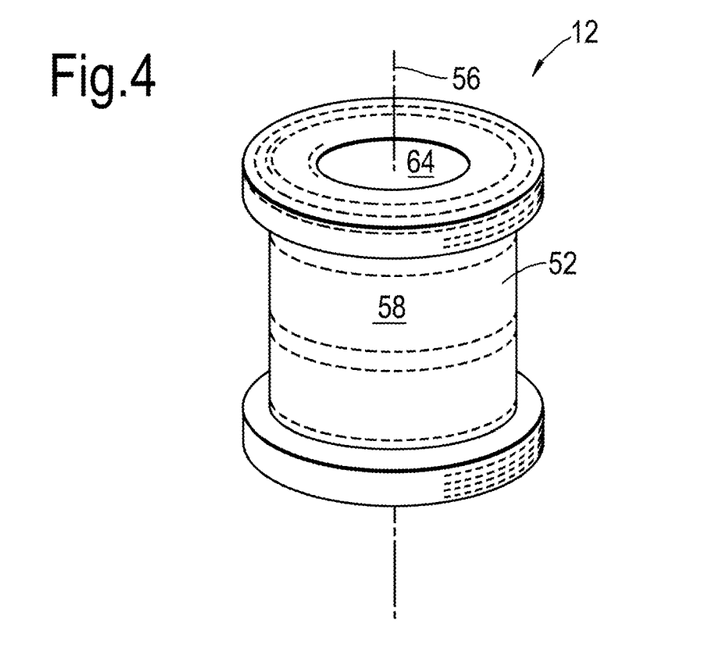
FIG. 4 illustrates a perspective view of an object according to various examples.
Figure 5:
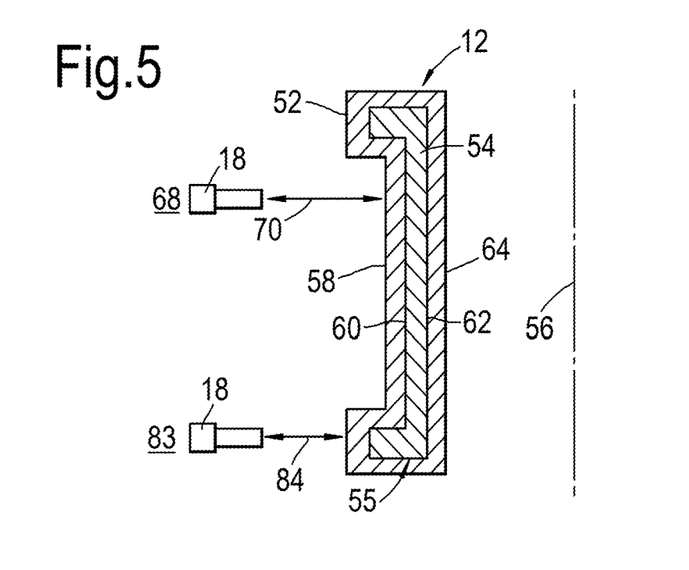
FIG. 5 illustrates a cross sectional side view of a part of the object illustrated in FIG. 4.

As illustrated in FIGS. 4 and 5, the object 12 may comprise a canister 52 and a combustor casing 54 for a gas turbine engine. The canister 52 defines a cavity 55 in which powder may be deposited and then diffusion bonded using a hot pressing process or a hot isostatic pressing process to form the combustor casing 54. The canister 52 and the combustor casing 54 are generally cylindrical in shape and have a longitudinal axis 56. The object 12 includes a first external surface 58 (defining a surface of the canister 52), a second internal surface 60 (defining a surface of the combustor casing 54), a third internal surface 62 (defining a surface of the combustor casing 54), and a fourth external surface 64 (defining a surface of the canister 52).

The operation of the apparatus 10 is described in the following paragraphs with reference to the flow diagrams illustrated in FIGS. 6, 9, 10, and 11.

Figure 6:
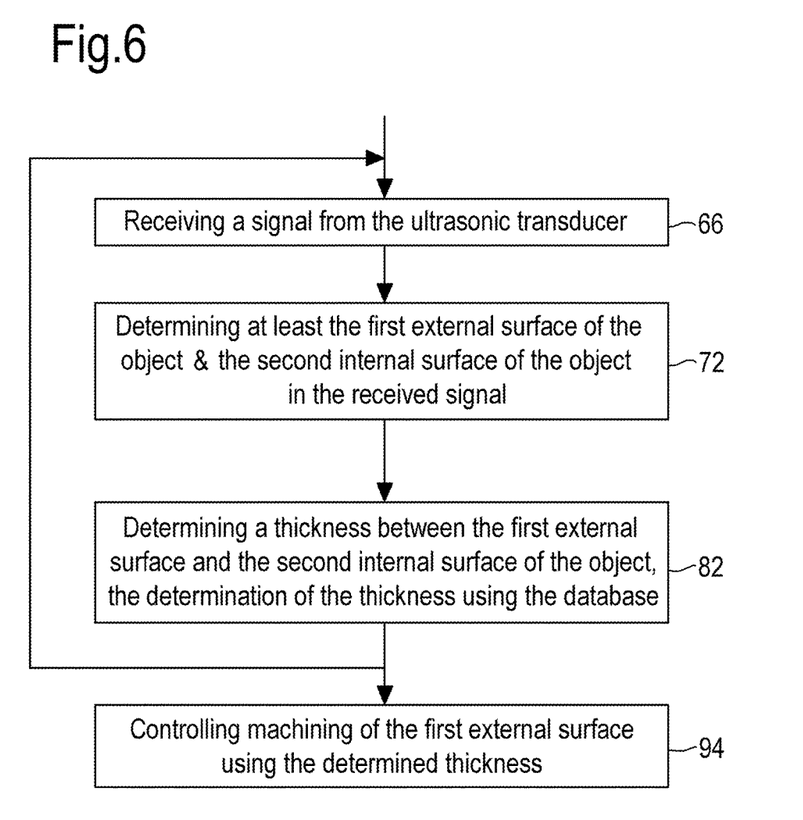
FIG. 6 illustrates a flow diagram of a method of machining an object according to various examples.

FIG. 6 illustrates a flow diagram of a method of machining the object 12 according to various examples.

At block 66, the method includes receiving a signal from the ultrasonic transducer 18 at a first position. For example, the controller 14 may control the first actuator 16 to move the ultrasonic transducer 18 to position 68 illustrated in FIG. 5. The controller 14 may then control the ultrasonic transducer 18 (or another ultrasonic transducer) to transmit an ultrasonic wave 70 towards the object 12. The ultrasonic transducer 18 may then receive the reflected ultrasonic wave 70 and convert the received ultrasonic wave 70 into a signal. The controller 14 then receives the signal from the ultrasonic transducer 18.

At block 72, the method includes determining at least the first external surface of the object and the second internal surface of the object in the received signal. For example, the controller 14 may receive the signal illustrated in FIG. 7 at block 66 and then determine at least the first external surface 58 and the second internal surface 60 of the object 12 illustrated in FIGS. 4 and 5.

Figure 7:
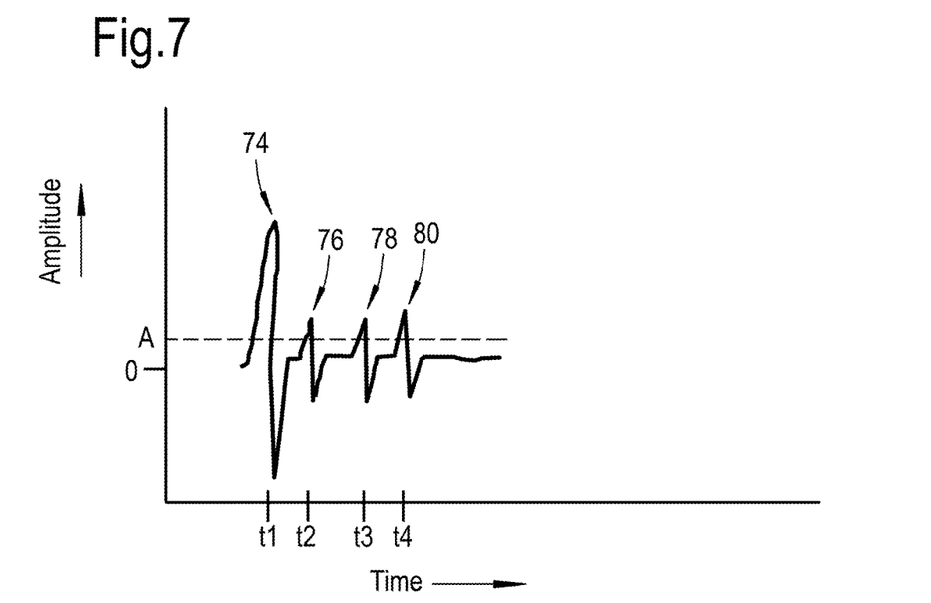
FIG. 7 illustrates a graph of amplitude versus time for an acoustic wave traversing through the object illustrated in FIGS. 4 and 5.

In more detail, FIG. 7 illustrates a graph having a horizontal axis for time, a vertical axis for amplitude, and a line illustrating how the amplitude of the received signal varies with time. The line has a first peak 74 at a time t1, a second peak 76 at a time t2, a third peak 78 at a time t3, and a fourth peak 80 at a time t4. The first, second, third and fourth peaks 74, 76, 78, 80 correspond to the first, second, third and fourth surfaces 58, 60, 62, 64 respectively since interfaces cause increased reflection of the ultrasonic wave 70. The controller 14 may determine at least the first external surface 58 and the second internal surface 60 by determining where the line has a peak with an amplitude greater than an amplitude of A.

At block 82, the method includes determining a thickness between at least the first external surface and the second internal surface of the object 12, the determination of the thickness using the database 44. For example, the controller 14 may determine the thickness between the first external surface 58 and the second internal surface 60 at position 68 by first determining the time period between the first peak 74 and the second peak 76 (which is equal t2−t1). Secondly, the controller 14 may select an acoustic wave velocity from the database 44 for the material between the first external surface 58 and the second internal surface 60 (the controller 14 having knowledge of the material by virtue of the materials of the object 12 being stored in the memory 36 or being received from the user input device 28). For example, where the material between the first external surface 58 and the second internal surface 60 is material A, the controller 14 may select an acoustic wave velocity of 1000 meters per second from the database 44 illustrated in FIG. 2. Third, the controller 14 may determine the thickness between the first external surface 58 and the second internal surface 60 by multiplying the selected acoustic wave velocity and the time period between the first peak 74 and the second peak 76. The controller 14 may store the determined thickness in the memory 36 as data 85.

In some examples, the controller 14 may additionally determine another parameter associated with the first material. For example, where the database 44 stores data for the acoustic wave velocity at reference temperatures in the respective materials in unstressed conditions, the controller 14 may be configured to relate localised variations in ultrasonic signal Time of Flight to strain energy. The controller 14 may be configured to provide positional and topographically relative information of the form "high tensile strain here, with a vector" or "compressive strain around here".

The controller 14 may then control the first actuator 16 to move the ultrasonic transducer 18 to a second position (different to the first position) relative to the object 12. For example, the controller 14 may control the first actuator 16 to move the ultrasonic transducer 18 to position 83 illustrated in FIG. 5. The method may then return to block 66 and be repeated for the ultrasonic transducer 18 at position 83.

At block 66, the method includes receiving a signal from the ultrasonic transducer 18 while the ultrasonic transducer 18 is positioned at position 83. For example, the controller 14 may control the ultrasonic transducer 18 (or another ultrasonic transducer) to transmit an ultrasonic wave 84 towards the object 12. The ultrasonic transducer 18 may then receive the reflected ultrasonic wave 84 and convert the received ultrasonic wave 84 into a signal. The controller 14 then receives the signal from the ultrasonic transducer 18.

At block 72, the method includes determining at least the first external surface of the object and the second internal surface of the object in the received signal. While at position 83, the controller 14 may receive the signal illustrated in FIG. 8 at block 66 and then determine at least the first external surface 58 and the second internal surface 60 of the object 12 illustrated in FIGS. 4 and 5.

Figure 8:
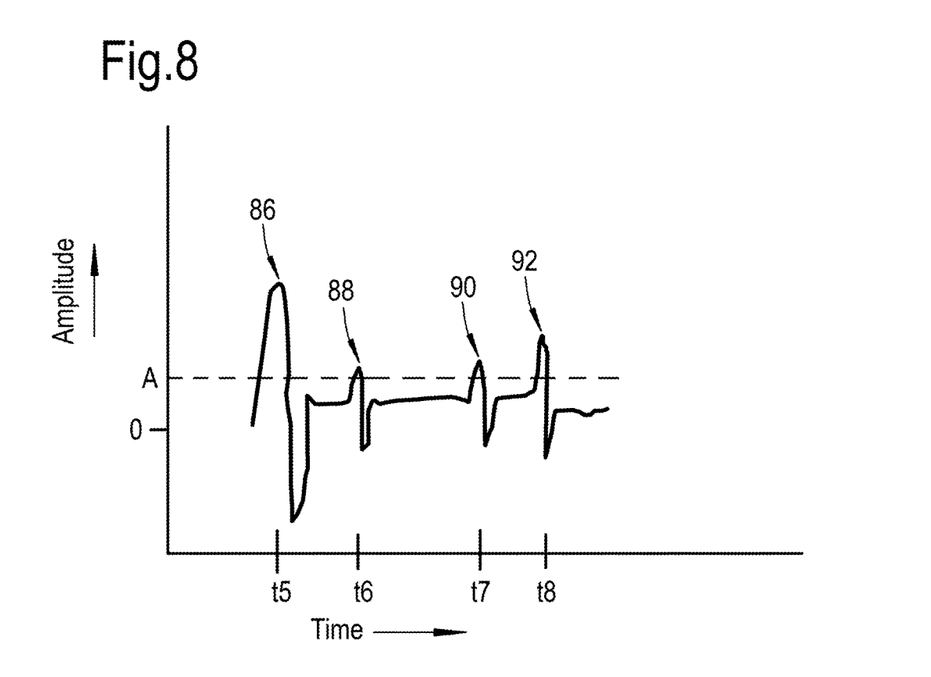
FIG. 8 illustrates another graph of amplitude versus time for an acoustic wave traversing through the object illustrated in FIGS. 4 and 5.

In more detail, FIG. 8 illustrates a graph having a horizontal axis for time, a vertical axis for amplitude, and a line illustrating how the amplitude of the received signal varies with time. The line has a first peak 86 at a time t5, a second peak 88 at a time t6, a third peak 90 at a time t7, and a fourth peak 92 at a time t8. The first, second, third and fourth peaks 86, 88, 90, 92 correspond to the first, second, third and fourth surfaces 58, 60, 62, 64 respectively at position 83. The controller 14 may determine at least the first external surface 58 and the second internal surface 60 by determining where the line has a peak with an amplitude greater than an amplitude of A.

At block 82, the method includes determining a thickness between at least the first external surface and the second internal surface of the object 12, the determination of the thickness using the database 44. For example, the controller 14 may determine the thickness between the first external surface 58 and the second internal surface 60 at position 83 by first determining the time period between the first peak 86 and the second peak 88 (which is equal t6–t5). Secondly, the controller 14 selects an acoustic wave velocity from the database 44 for the material between the first external surface 58 and the second internal surface 60. Third, the controller 14 determines the thickness between the first external surface 58 and the second internal surface 60 by multiplying the selected acoustic wave velocity and the time period between the first peak 88 and the second peak 86. The controller 14 may store the determined thickness in the memory 36 as data 85.

When the controller 14 determines that sufficient measurements of thickness have been performed, the method moves to block 94. The controller 14 may determine that a sufficient number of measurements of thickness have been performed when the number of measurements is equal to a threshold number of measurements. Alternatively, the controller 14 may determine that a sufficient number of measurements of thickness have been performed when the controller 14 receives a signal from the user input device 28 indicating that a sufficient number have been performed.

At block 94, the method includes controlling machining of the first external surface using the determined thickness. For example, the controller 14 may use the determined thickness to avoid contact between the machine tool 26 and the second internal surface 60. By way of an example, where the machine tool 26 is a contact tool (such as a milling machine or a grinding machine) the controller 14 may control the second actuator 24 to move the machine tool 26 into contact with the first external surface 58 of the object 12. The controller 14 may also control the machine tool 26 to operate so that at least a portion of the first external surface 58 is removed. By way of another example, where the machine tool 26 is a liquid cutting apparatus (such as a water jet cutter), the controller 14 may control the second actuator 24 to move the liquid cutting apparatus 26 to a desired position (position 68 or 83 illustrated in FIG. 5 for example). The controller 14 may then control the liquid cutting apparatus 26 to provide a jet of liquid for machining the first external surface 58.

At block 94, the controller 14 may use the material type, thickness and position to generate a machine tool 26 path plan so as to anticipate the change in cutting parameters including cutting depths and expected force feedback.

Where the controller 14 is configured to determine strain energy in the object 12, the controller 14 may generate an adaptive machine tool cutting path so as to get closer to the ideal final profile geometry. In other words, this knowledge of potential for distortion may advantageously inform more effective machining paths to achieve the desired end geometry (after the deflection has been accounted for).

The method may then return to block 66 so that the machined surfaces of the object 12 may be inspected and machined once again if necessary.

The apparatus 10 may provide several advantages. First, the apparatus 10 may provide improved machining of an object 12 since the controller 14 may use the determined thickness of the material between the first external surface 58 and the second internal surface 60 to ensure that the second internal surface 60 is not machined and protrusions of the second material (bosses for example) are avoided by the machine tool 26. Second, the machine tool 26 may advantageously require replacement and/or repair less often since the machine tool 26 is less likely to collide with the second internal surface 60 during machining and be damaged by the collision. Third, where the ultrasonic transducer 18 and the machine tool 26 are implemented on the same machine (or are integrated together), the operation of the apparatus 10 may require less time since movement of the object 12 between the ultrasonic transducer 18 and the machine tool 26 may not be necessary.

Figure 9:
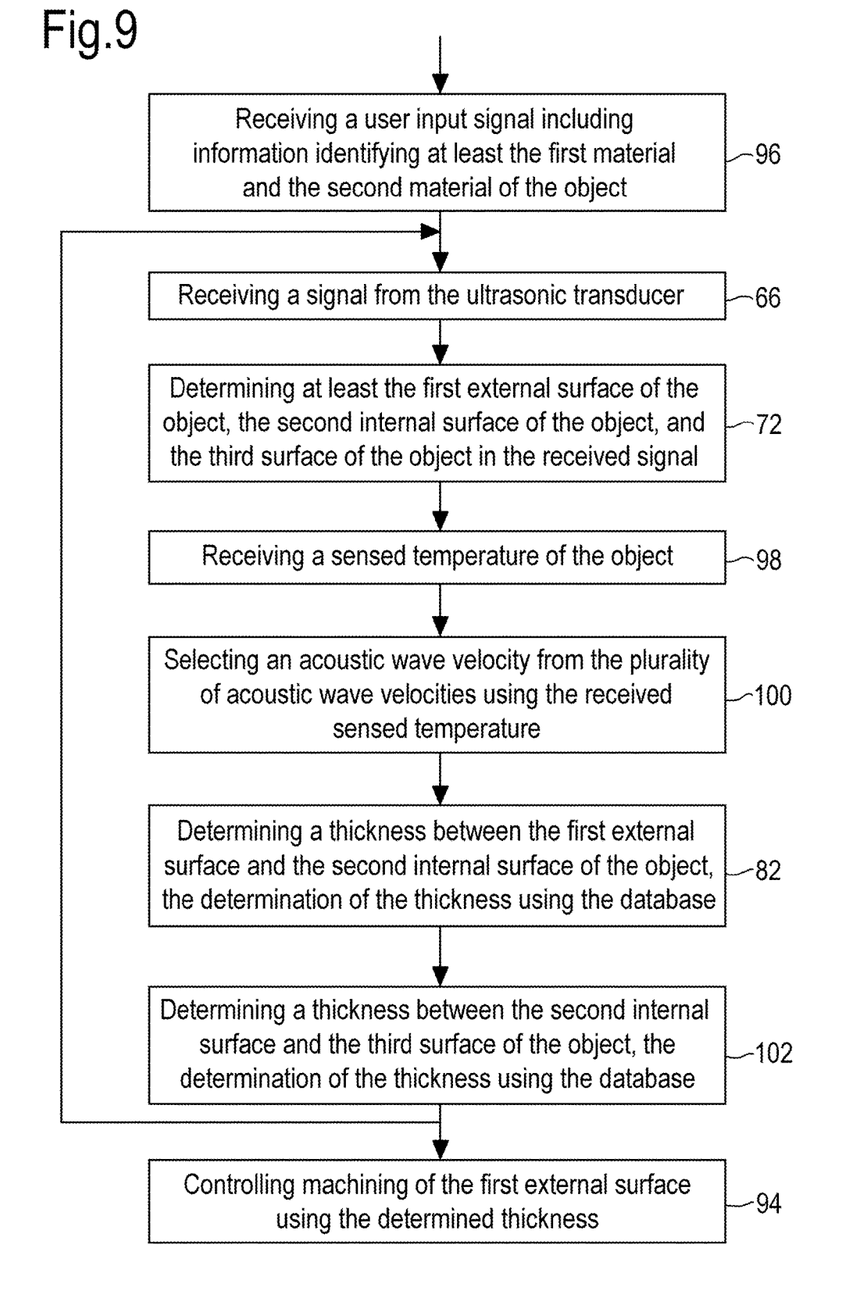
FIG. 9 illustrates a flow diagram of another method of machining an object according to various examples.

FIG. 9 illustrates a flow diagram of another method of machining an object 12 according to various examples. The method illustrated in FIG. 9 is similar to the method illustrated in FIG. 6, and where the blocks are similar, the same reference numerals are used.

At block 96, the method includes receiving a user input signal including information identifying at least the first material and the second material of the object 12. For example, the controller 14 may control a display of the output device 30 to display a plurality of different materials (those stored within the database 44) and an operator may use the user input device 28 to select the first and second materials.

At block 66, the method includes receiving a signal from the ultrasonic transducer 18 while the ultrasonic transducer 18 is located at a first position (for example, position 68 illustrated in FIG. 5).

At block 72, the method includes determining at least the first external surface of the object 12, the second internal surface of the object 12 and the third surface of the object 12 in the signal received at block 66. For example, the controller 14 may receive the signal illustrated in FIG. 7 at block 66 and then determine at least the first external surface 58, the second internal surface 60, and the third internal surface 62 (and may also determine the fourth external surface 64) of the object 12 illustrated in FIGS. 4 and 5.

At block 98, the method includes receiving a sensed temperature of the object 12. For example, the controller 14 may receive a signal from the temperature sensor 20 that includes the sensed temperature of the object 12 and/or the liquid 33 in the container 32.

At block 100, the method includes selecting an acoustic wave velocity from the plurality of acoustic wave velocities using the received sensed temperature. For example, the controller 14 may use the sensed temperature received at block 98 to interrogate the database 44 and select acoustic wave velocities for the first and second materials of the object 12. By way of an example, where materials A and C have been selected at block 96, and the controller 14 has received a sensed temperature of 20 Celsius, the controller 14 selects an acoustic wave velocity of 1000 meters per second for material A, and an acoustic wave velocity of 1550 meters per second for material C, from the database 44 illustrated in FIG. 3.

At block 82, the method includes determining a thickness between the first external surface and the second internal surface of the object 12 using the database 44. For example, the controller 14 may determine a thickness between the first external surface 58 and the second internal surface 60 of the object 12 illustrated in FIGS. 4 and 5 as described in the preceding paragraphs.

At block 102, the method includes determining a thickness between the second internal surface and the third surface of the object 12 using the database 44. For example, the controller 14 may determine the thickness between the second internal surface 60 and the third internal surface 62 at position 68 by determining the time period between the second peak 76 and the third peak 78 (which is equal t3–t2). The controller 14 may then determine the thickness by multiplying the acoustic wave velocity selected at block 100 and the time period between the second peak 76 and the third peak 78. The controller 14 may then store the determined thickness in the memory 36 as data 85.

At block 102, the method may also include determining a thickness between the third internal surface 62 and the fourth external surface 64 (and any other layers of material of the object 12) at position 68.

The controller 14 may then control the first actuator 16 to move the ultrasonic transducer 18 to a second position (different to the first position) relative to the object 12. For example, the controller 14 may control the first actuator 16 to move the ultrasonic transducer 18 to position 83 illustrated in FIG. 5. The method may then return to block 66 and be repeated for the ultrasonic transducer 18 at position 83 to determine the thickness between the first external surface 58 and the second internal surface 60, and the thickness between the second internal surface 60 and the third internal surface 62 (and any other layers of material of the object 12).

When the controller 14 determines that sufficient measurements of thickness have been performed, the method moves to block 94.

At block 94, the method includes controlling machining of the first external surface using the determined thickness. For example, the controller 14 may use the determined thickness to avoid contact between the machine tool 26 and the second internal surface 60.

The method may then return to block 66 so that the machined surfaces of the object 12 may be inspected and machined once again if necessary. The controller 14 may also measure the determined thickness between the second internal surface 60 and the third internal surface 62 to investigate whether the determined thickness has fallen below a threshold thickness.

The method illustrated in FIG. 9 may advantageously provide an accurate determination of the thicknesses of the layers of the object 12 since the temperature of the object 12 (or the liquid 33) is determined and used to select associated acoustic wave velocities from the database 44.

Figure 10:
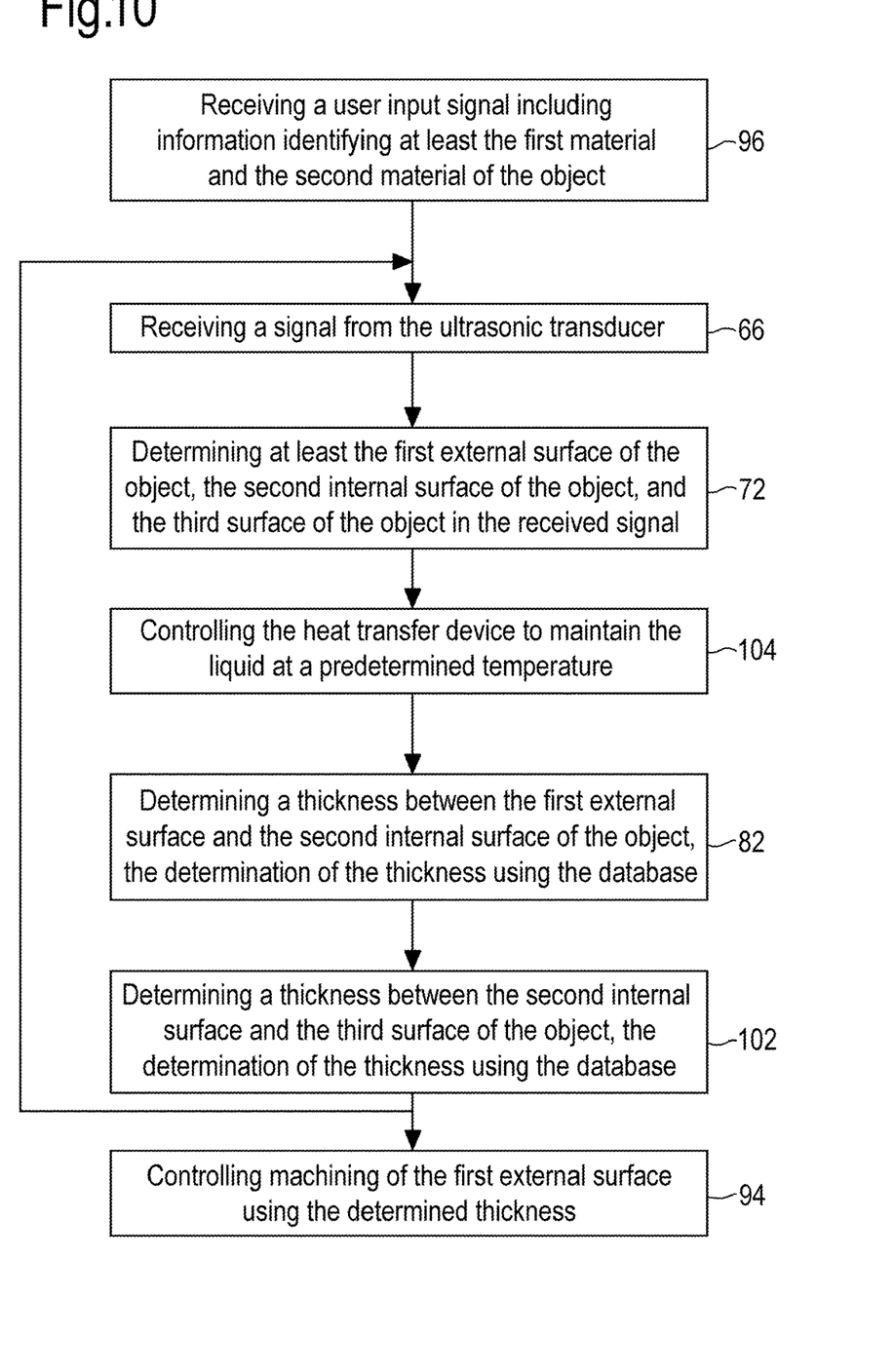
FIG. 10 illustrates a flow diagram of a further method of machining an object according to various examples.

FIG. 10 illustrates a flow diagram of a further method of machining an object 12 according to various examples. The method illustrated in FIG. 10 is similar to the methods illustrated in FIGS. 6 and 9 and where the features are similar, the same reference numerals are used.

At block 96, the method includes receiving a user input signal including information identifying at least the first material and the second material of the object 12.

At block 66, the method includes receiving a signal from the ultrasonic transducer 18 at a first position (such as position 68 illustrated in FIG. 5).

At block 72, the method includes determining at least the first external surface of the object 12, the second internal surface of the object 12, and may also include determining the third surface of the object 12 in the received signal.

At block 104, the method includes controlling the heat transfer device 22 to maintain the liquid 33 at a predetermined temperature. For example, the controller 14 may control the heat transfer device 22 to heat and/or cool the liquid 33 so that the temperature of the liquid 33 remains static. In other examples, the controller 14 may control the heat transfer device 22 to heat and/or cool the object 12 directly (for example, using an infrared heater) so that the object 12 remains at a static, predetermined temperature.

At block 82, the method includes determining a thickness between the first external surface and the second internal surface of the object 12 using the database 44. For example, the controller 14 may determine the thickness by selecting an acoustic wave velocity from the database 44 illustrated in FIG. 3 at the predetermined temperature of the object 12 mentioned above at block 104.

At block 102, the method may include determining a thickness between the second internal surface and the third surface of the object 12 using the database 44. As mentioned above for block 82, the controller 14 may determine the thickness by selecting an acoustic wave velocity from the database 44 illustrated in FIG. 3 at the predetermined temperature of the object 12.

The controller 14 may then control the first actuator 16 to move the ultrasonic transducer 18 to a different position relative to the object 12. For example, the controller 14 may control the first actuator 16 to move the ultrasonic transducer 18 to position 83 illustrated in FIG. 5. The method may then return to block 66 and be repeated for the ultrasonic transducer 18 at position 83 to determine the thickness between the first external surface 58 and the second internal surface 60, and optionally, the thickness between the second internal surface 60 and the third internal surface 62 (and any other layers of material of the object 12).

When the controller 14 determines that sufficient measurements of thickness have been performed, the method moves to block 94.

At block 94, the method includes controlling machining of the first external surface using the determined thickness. For example, the controller 14 may use the determined thickness to avoid contact between the machine tool 26 and the second internal surface 60.

The method may then return to block 66 so that the machined surfaces of the object 12 may be inspected and machined once again if necessary. The controller 14 may also measure the determined thickness between the second internal surface 60 and the third internal surface 62 to investigate whether the determined thickness has fallen below a threshold thickness through machining.

The method illustrated in FIG. 10 may advantageously provide an accurate determination of the thicknesses of the layers of the object 12 since the temperature of the object 12 (or the liquid 33) is maintained at a static temperature and may consequently result in accurate acoustic wave velocities being selected from the database 44.

Figure 11:
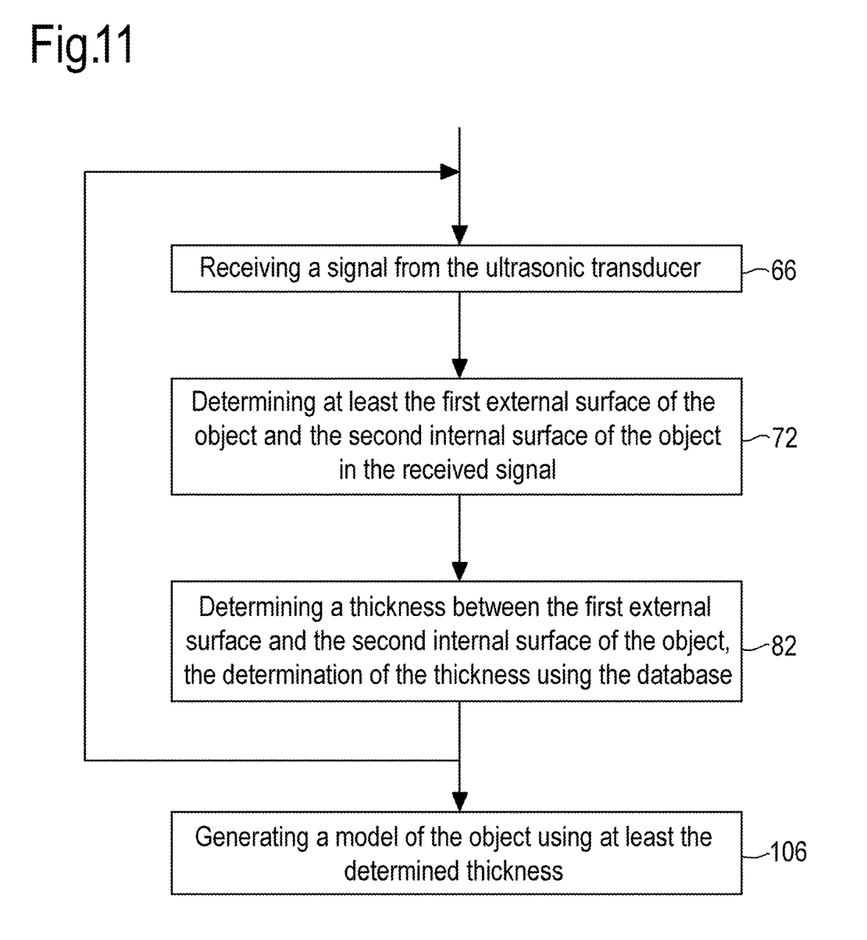
FIG. 11 illustrates a flow diagram of a method of inspecting an object according to various examples.

FIG. 11 illustrates a flow diagram of a method of inspecting an object 12 according to various examples. The method illustrated in FIG. 11 is similar to the method illustrated in FIG. 6 and where the features are similar, the same reference numerals are used.

At block 66, the method includes receiving a signal from the ultrasonic transducer 18 while the ultrasonic transducer 18 is located at a first position (such as position 68 illustrated in FIG. 5).

At block 72, the method includes determining at least the first external surface of the object 12 and the second internal surface of the object 12 in the received signal.

At block 82, the method includes determining a thickness between the first external surface and the second internal surface of the object 12 using the database 44. The determined thickness may be stored in the memory 36 as data 85.

The controller 14 may then control the first actuator 16 to move the ultrasonic transducer 18 to a second (and different) position relative to the object 12. For example, the controller 14 may control the first actuator 16 to move the ultrasonic transducer 18 to position 83 illustrated in FIG. 5. The method may then return to block 66 and be repeated for the ultrasonic transducer 18 at position 83 to determine the thickness between the first external surface 58 and the second internal surface 60, When the controller 14 determines that sufficient measurements of thickness have been performed, the method moves to block 106.

At block 106, the method includes generating a model of the object 12 using at least the determined thickness or thicknesses. For example, the controller 18 may use the data 85 for the determined thicknesses stored in the memory 36 to generate a two dimensional model (such as a cross section) or a three dimensional model of the object 12. The controller 14 may control the output device 30 to present the generated model to the operator. For example, the controller 14 may control a printer of the output device 30 to print at least a portion or one perspective of the model on a printing substrate. By way of another example, the controller 14 may control a display of the output device 30 to display an image of at least a part of the model. An operator may use the user input device 28 to manipulate the image of the model on the display.

The method illustrated in FIG. 11 may advantageously enable an operator to inspect the object 12 and determine whether internal layers have desired thicknesses.

It will be understood that the invention is not limited to the embodiments above-described and various modifications and improvements can be made without departing from the concepts described herein. For example, block 106 (generating a model of the object 12 using at least the determined thickness) may be performed in any of the methods illustrated in FIGS. 6, 9 and 10.

Except where mutually exclusive, any of the features may be employed separately or in combination with any other features and the disclosure extends to and includes all combinations and sub-combinations of one or more features described herein.

The invention claimed is:

1. A method of machining an object, the method comprising:
   receiving a signal from an ultrasonic transducer;
   determining at least a first external surface of the object and a second internal surface of the object in the received signal;
   determining a thickness between the first external surface and the second internal surface of the object, the object comprising a first material between the first external surface and the second internal surface, and a second material between the second internal surface and a third surface, the determination of the thickness using a database including a plurality of materials and a plurality of associated acoustic wave velocities; and
   controlling machining of the first external surface using the determined thickness.

2. The method according to claim 1, further comprising: determining the third surface of the object in the received signal; and determining a thickness between the second internal surface and the third surface using the database.

3. The method according to claim 1, wherein the third surface is an external surface of the object.

4. The method according to claim 1, wherein the third surface is an internal surface of the object.

5. The method according to claim 1, wherein the database further comprises a plurality of temperatures for at least some of the plurality of materials, the plurality of acoustic wave velocities being associated with the plurality of temperatures.

6. The method according to claim 5, further comprising: receiving a sensed temperature of the object; and selecting an acoustic wave velocity from the plurality of acoustic wave velocities using the received sensed temperature to determine the thickness between the first external surface and the second internal surface.

7. The method according to claim 1, wherein the object is at least partially immersed in a liquid, the method further comprising: controlling a heat transfer device to maintain the liquid at a predetermined temperature, the acoustic wave velocities in the database being acoustic wave velocities in the plurality of materials at the predetermined temperature.

8. The method according to claim 1, further comprising receiving a user input signal including information identifying at least the first material and the second material of the object.

9. The method according to claim 1, wherein controlling machining of the first external surface includes controlling a tool to remove at least a part of the first material from the object.

10. The method according to claim 1, wherein controlling machining of the first external surface includes controlling a water jet cutter to machine the object, the ultrasonic transducer being integrated with the water jet cutter.

11. The method according to claim 1, wherein the object is formed using a hot isostatic pressing process.

12. A method of inspecting an object, the method comprising:
   receiving a signal from an ultrasonic transducer;
   determining at least a first external surface of the object and a second internal surface of the object in the received signal; and
   determining a thickness between the first external surface and the second internal surface of the object, the object comprising a first material between the first external surface and the second internal surface, and a second material between the second internal surface and a third surface, the determination of the thickness using a database including a plurality of materials and a plurality of associated acoustic wave velocities.

13. The method according to claim 12, further comprising generating a model of the object using at least the determined thickness.

14. Apparatus comprising a controller configured to perform the method according to claim 1.

* * * * *